(12) United States Patent
Feist et al.

(10) Patent No.: US 8,193,388 B2
(45) Date of Patent: Jun. 5, 2012

(54) COMPOUNDS FOR DEPOSITING TELLURIUM-CONTAINING FILMS

(75) Inventors: Benjamin J. Feist, Wilmington, DE (US); Christian Dussarrat, Wilmington, DE (US)

(73) Assignee: American Air Liquide, Inc., Fremont, CA (US)

( * ) Notice: Subject to any disclaimer, the term of this patent is extended or adjusted under 35 U.S.C. 154(b) by 370 days.

(21) Appl. No.: 12/423,382

(22) Filed: Apr. 14, 2009

(65) Prior Publication Data

US 2009/0256127 A1    Oct. 15, 2009

Related U.S. Application Data

(60) Provisional application No. 61/045,179, filed on Apr. 15, 2008.

(51) Int. Cl.
*C07C 395/00* (2006.01)
*C07D 293/00* (2006.01)
*H01L 21/06* (2006.01)

(52) U.S. Cl. ............... 562/899; 257/E21.068; 438/102; 544/1

(58) Field of Classification Search .................. 562/899; 544/1; 438/102; 257/E21.068
See application file for complete search history.

(56) References Cited

U.S. PATENT DOCUMENTS

2009/0074652 A1    3/2009  Dussarrat
2009/0087561 A1    4/2009  Chen et al.
2009/0215225 A1    8/2009  Stender et al.

FOREIGN PATENT DOCUMENTS

WO    WO 2008057616    5/2008

OTHER PUBLICATIONS

Ma et al., Transactions of Nonferrous Metal Society of China, vol. 16, No. 3, pp. 693-699 (2006).*
Bjorgvinsson, Mar, et al., "Preparation and Structural Characterization of the Bis[bis(trimethylsilyl)amido] chalcogenides of Selenium and Tellurium," Inorg. Chem., 1990, 29, 5140-5143.
Chivers, Tristram, et al, "Tellurium—Nitrogen Double Bonds and a Novel Te3N3 Ring: Formation and Structures of [(tBuNH)(tBuN)3Te2]Cl, [tBuNTeNtBu]2, and [tBuNTe]3," J. Am. Chem. Soc., 1995, 117, 2359-2360.
Choi, Buyng Joon, et al., "Combined Atomic Layer and Chemical Vapor Deposition, and Selective Growth of Ge2Sb2Te5 Films on TiN/W Contact Plug," Chem. Mater. 2007, 19, 4387-4389.
Irgolic, Kurt J., "The Organic Chemistry of Tellurium," Dept. of Chem., Texas A&M Univ., 1974, 3 pgs.
McGeachin, S.G., "Synthesis and Properties of some β-diketimines derived from acetylacetone, and their metal complexes," Canadian Journal of Chemistry, vol. 46, 1968, pp. 1903-1912.
Renson, Marcel, "The Chemistry of organic selenium and tellurium compounds," Wiley, New York, 1986, vol. 1, pp. 399-449.

* cited by examiner

*Primary Examiner* — Porfirio Nazario Gonzalez
(74) *Attorney, Agent, or Firm* — Patricia E. McQueeney

(57) ABSTRACT

Disclosed herein are tellurium metal-organic precursors and methods for depositing tellurium-containing films on a substrate.

15 Claims, 2 Drawing Sheets

COMPOUNDS FOR DEPOSITING TELLURIUM-CONTAINING FILMS

CROSS REFERENCE TO RELATED APPLICATIONS

The present application claims the benefit of U.S. Provisional Application Ser. No. 61/045,179 filed Apr. 15, 2008, herein incorporated by reference in its entirety for all purposes.

BACKGROUND

Modifying substrates by coating the surfaces thereof in such a manner that the surface will have certain functional properties is known. For example, tellurium-containing films can be used in the formation of GST films (germanium-antimony-tellurium films, "GST" usually refers to $Ge_2Sb_2Te_5$, but may include other compositions such as GeSbTe$_2$) for the application of PRAM (Phase Change Random Access Memory). Furthermore, tellurium is used in combination with other metals for PRAM fabrication, such as InGe$_2$Te$_2$, AsSbTe, CrSbTe or MoSbTe.

The main industrial options to enable the deposition of such films with reasonable throughput and acceptable purity are deposition techniques, such as MOCVD (Metal-Organic Chemical Vapor Deposition) or ALD (Atomic Layer Deposition). Metal-organic or metal-halide precursors are required for those processes. The requirements for a metal-organic compound to be suitable for an industrial process include:
  being liquid at room temperature or having a low melting point for distribution considerations
  volatility; and
  thermal stability.

Various tellurium metal-organic compounds have been considered as precursors to enable such deposition. Examples include:
  Imines such as (tBuNTeNtBu)$_2$ and (tBuNTe)$_3$ have been reported by Chivers et al. (J. Am. Chem. Soc. 1995, 117, 2359); however, these precursors exist as dimers and trimers, acting to decrease the volatility of the molecule,
  Amines such as Te(N(SiMe$_3$)$_2$)$_2$ have been reported by Björgvinsson et al. (Inorg. Chem. 1990, 29, 5140); however, this precursor exhibits dimerism in the solid state, resulting in a decreased volatility over a monomer species.
  Diorganyl tellurides are also known in the literature (M. Renson, 'The Chemistry of Organic Selenium and Tellurium Compounds', Wiley, New York, 1986, Vol. 1, p. 399).
  Atomic layer deposition of GST films has been achieved by Choi et al. (Chem. Mater. 2007, 19 4387-4389) using the alkyl precursor Te(iPr)$_2$. Alkyl precursors have the benefit of higher volatility; however, the low decomposition temperature of Te(iPr)$_2$ (~200° C.) compared with the Sb and Ge precursor lead to a CVD-type behavior.
  Tellurium alkoxide precursors are known; however, they have significantly lower volatilities than alkyl precursors.
  Diorganyltellurium dihalides are known, however they exist as crystalline solids with low volatility (K. J. Irgolic, 'The Organic Chemistry of Tellurium', Gordon & Breach, New York, 1974). In addition, the potential for halogen contamination of the film presents halogen containing precursors as unattractive for the deposition process.

Thus, a need remains for suitable tellurium metal-organic compounds that enable the deposition of tellurium-containing films.

The tellurium metal-organic compounds must present the features of 1) being liquid or having a melting point below 80° C., 2) being volatile enough for use industrial ALD and/or MOCVD tools, and 3) enabling the deposition by MOCVD and ALD of metal containing films such as In$_x$Ge$_y$Te, $M^1_x$Sb$_y$Te$_z$, Sb$_x$Te$_y$, or CdTe, with $M^1$ being selected from but not limited to germanium, chromium, or arsenic.

SUMMARY

Disclosed are tellurium metal-organic compounds and methods for depositions of these compounds which may be used in the manufacture of semiconductor materials, photovoltaic, LCD-TFT, catalysts, or flat panel-type devices.

Also disclosed are tellurium metal-organic compounds containing either β-diketiminato ligands or β-ketoiminato ligands and having the general formula:

where:
  R represents substituted β-diketiminato of the general formula $R^1C(NR^4)CR^2C(NR^5)R^3$ or substituted β-ketoiminato of the general formula $R^1COCR^2C(NR^4)R^3$,
  $R^1$ and $R^3$ may be the same or different and represent a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl substituted phenyl, or an organosilyl, and $R^2$, $R^4$, and $R^5$ may be the same or different and represent hydrogen, halogen, a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl, or an organosilyl;
  each L is independently selected from the group consisting of a hydrocarbon, an oxygen-containing hydrocarbon, a nitrogen-containing hydrocarbon, an amine or polyamine, a bipyridine, a heterocycle containing oxygen or nitrogen, or any combination thereof;
  m represents an integer from 1 to 4; and
  n represents an integer from 0 to 4.

The disclosed tellurium metal-organic compounds may include one or more of the following aspects:
  R is $(R^1COCR^2C(NR^4)R^3)$, $R^1$ and $R^3$ are methyl, and $R^4$ is isopropyl.
  R is $(R^1C(NR^4)CR^2C(NR^5)R^3)$, $R^1$ and $R^3$ are methyl, and $R^4$ and $R^5$ are isopropyl.
  R represents $R^1C(NR^4)CR^2C(NR^5)R^3$, m is 2, and n represents an integer from 0 to 2, as depicted in the following formula:

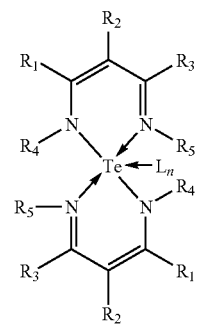

Te(pentane-2,4-diketiminato)$_2$, Te(N,N'-dimethylpentane-2,4-diketiminato)$_2$, Te(N,N'-diethylpentane-2,4-diketiminato)$_2$, Te(N,N'-diisopropylpentane-2,4-diketiminato)$_2$ R represents R$^1$COCR$^2$C(NR$^4$)R$^3$, m is 2, and n represents an integer from 0 to 2, as depicted in the following formula:

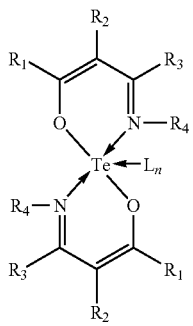

Te(pentane-2,4-ketoiminato)$_2$, Te(N-methylpentane-2,4-ketoiminato)$_2$, Te(N-ethylpentane-2,4-ketoiminato)$_2$, and Te(N-isopropylpentane-2,4-ketoiminato)$_2$ Further disclosed are methods of depositing tellurium-containing films on a substrate. The disclosed tellurium metal-organic compound is introduced into a reaction chamber containing at least one substrate and is contacted with the substrate to form a tellurium-containing film on at least one surface of the substrate using a deposition process.

The disclosed methods of depositing tellurium-containing films may include one or more of the following aspects:
- providing at least one reactant species into the reaction chamber with the metal-organic compound to form a reaction mixture and contacting the reactant mixture with the substrate.
- providing at least one reactant species into the reaction chamber and reacting the metal-organic compound with the reactant species.
- the metal-organic compound and the reactant species may either be introduced at least partially simultaneously, as in a chemical vapor deposition process, or at least partially sequentially, as in an atomic layer deposition process.
- the temperature of the reaction chamber may range between 100 to 500° C.
- the temperature of the reaction chamber may range between 150 and 350° C.
- the deposition process may be a chemical vapor deposition process.
- the deposition process may be an atomic layer deposition process having a plurality of deposition cycles.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

NOTATION AND NOMENCLATURE

Certain terms are used throughout the description and claims to refer to particular chemical constituents.

As used herein, the abbreviation "tBu" refers to a tertiary butyl group; the abbreviation "Me" refers to a methyl group; the terms "alkyl" or "alkyl group" refer to saturated functional groups containing exclusively carbon and hydrogen atoms; the abbreviation "iPr" refers to an isopropyl group; the abbreviation "TMA" refers to trimethyl aluminum; the abbreviation "TBTDET" refers to tertiary butylimido, tris(diethylamino) tantalum (Ta[N(C$_2$H$_5$)$_2$]$_3$[NC(CH$_3$)$_3$]); the abbreviation "TAT-DMAE" refers to tantalum tetraethoxide dimethylaminoethoxide; the abbreviation "PET" refers to pentaethoxy tantalum, the abbreviation "TBTDEN" refers to tertiary butylimido, tris(diethylamino) niobium; the abbreviation "PEN" refers to pentaethoxy niobium; the abbreviation "Ln" refers to the lanthanide group, which includes the following elements: scandium ("Sc"), yttrium ("Y"), lanthanum ("La"), cerium ("Ce"), praseodymium ("Pr"), neodymium ("Nd"), samarium ("Sm"), europium ("Eu"), gadolinium ("Gd"), terbium ("Tb"), dysprosium ("Dy"), holmium ("Ho"), erbium ("Er"), thulium ("Tm"), ytterbium ("Yb"), or lutetium ("Lu"); the abbreviation "tmhd" refers to 2,2,6,6-tetramethylheptane-3,5-dionate; the abbreviation "TriDMAS" refers to tris(dimethylamino) silane [SiH(NMe$_2$)$_3$]; the abbreviation "BDMAS" refers to bis(dimethylamino) silane; the abbreviation "BDEAS" refers to bis(diethylamino) silane [SiH$_2$(NEt$_2$)$_2$]; the abbreviation "TDEAS" refers to tetrakis-diethylamino silane; the abbreviation "TDMAS" refers to tris(dimethylamino) silane; the abbreviation "TEMAS" refers to tetrakis-ethylmethylamino silane (Si(N(C$_2$H$_5$)(CH$_3$))$_4$); the abbreviation "BTBAS" refers to bis(tert-butylamino)silane [SiH$_2$(NHtBu)$_2$]; the abbreviation "pda" refers to pentane-2,4-diketiminato; the abbreviation "sccm" refers to standard cubic centimeters per minute.; the group V metals refer to V, Nb, and Ta; the group VI metals refer to Cr, Mo, and W.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
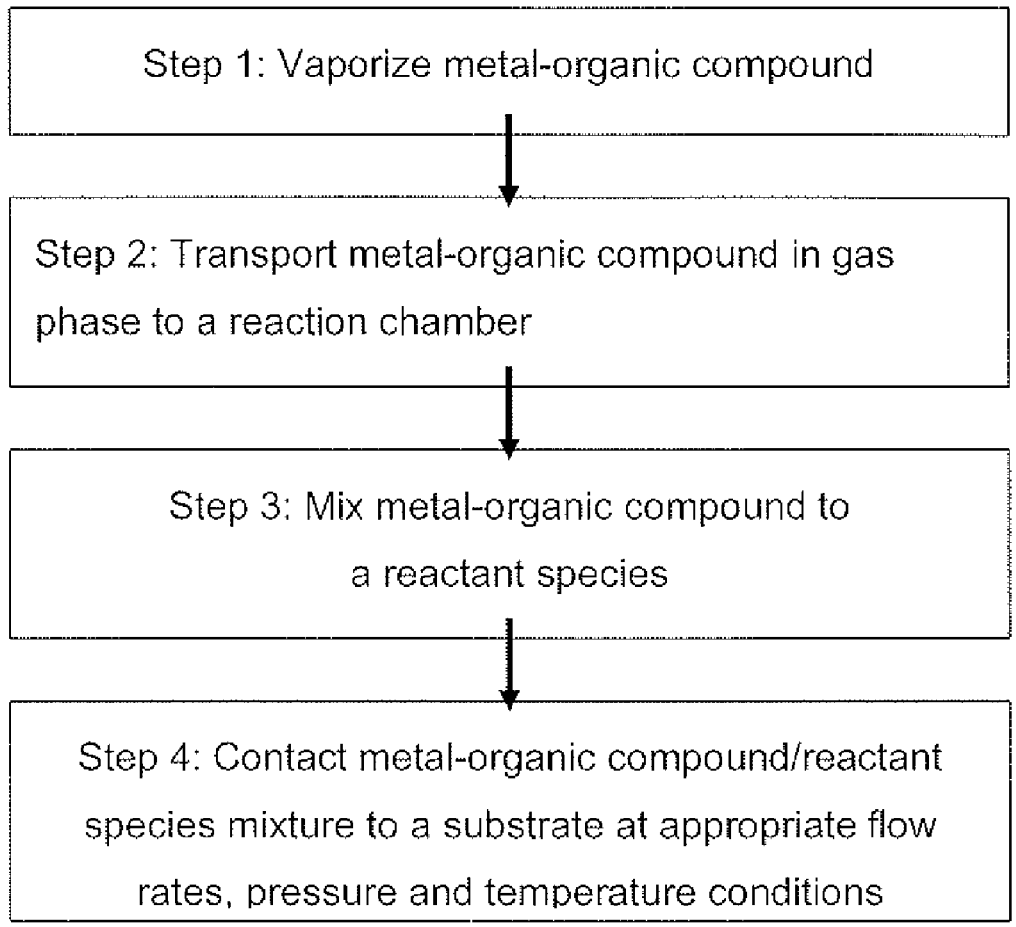
FIG. 1 is a flow chart of one exemplary deposition process through which the disclosed tellurium metal-organic compound may proceed to deposit a tellurium containing film on a substrate.

It has now been found that the disclosed tellurium metal-organic compounds present particularly attractive thermal properties. The proposed new precursors present the advantages of 1) being liquid at room temperature or having a melting point lower than 80° C., 2) having sufficient thermal stability to enable proper distribution (gas phase or direct liquid injection) without generation of particles, 3) having sufficient thermal stability to allow wide self-limited ALD window, and 4) allowing for the deposition of a variety of late transition metal containing films, including ternary or quaternary materials, by using one or a combination of co-reactants.

The disclosed tellurium metal-organic compounds contain either β-diketiminato ligands or β-ketoiminato ligands and have the general formula

where:
R represents substituted β-diketiminato of the general formula $R^1C(NR^4)CR^2C(NR^5)R^3$ or substituted β-ketoiminato of the general formula $R^1COCR^2C(NR^4)R^3$,
$R^1$ and $R^3$ may be the same or different and represent a linear or branched alkyl having from 1 to 5 carbon atoms, halogen-substituted linear or branched alkyl having from 1 to 7 carbon atoms, an alkylamide having from 1 to 4 carbons, an alkoxide having from 1 to 4 carbons, an aryl substituted phenyl, or an organosilyl, and $R^2$, $R^4$, and $R^5$ may be the same or different and represent hydrogen, halogen, linear or branched alkyl having from 1 to 5 carbon atoms, halogen-substituted linear or branched alkyl having from 1 to 7 carbon atoms, an alkylamide having from 1 to 4 carbons, an alkoxide having from 1 to 4 carbons, an aryl, or an organosilyl;
each L is independently selected from the group consisting of a hydrocarbon, an oxygen-containing hydrocarbon, a nitrogen-containing hydrocarbon, an amine or polyamine, a bipyridine, a heterocycle containing oxygen or nitrogen, or any combination thereof;
m represents an integer from 1 to 4; and
n represents an integer from 0 to 4.

The disclosed compounds preferably have a melting point lower than 80° C., i.e. which are liquid or may be easily liquefied for delivery. More preferably the disclosed compounds have a melting point lower than 35° C.

The disclosed compounds preferably have a vapor pressure higher than 1 Torr at 25° C.

Preferred compounds have either of the following general formulae

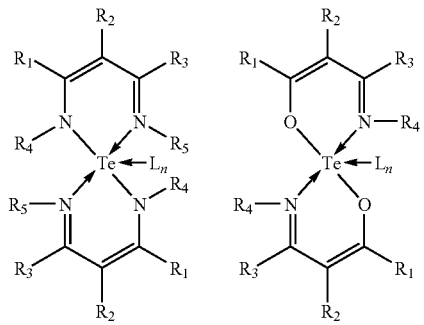

wherein:
$R^1$ and $R^3$ represent an alkyl which optionally is substituted with halogen, said alkyl having been selected from methyl, ethyl, propyl, butyl, pentyl, isopropyl, isobutyl, sec-butyl, t-butyl, and neopentyl, phenyl, tolyl, trimethylsilyl or triethylsilyl;
$R^2$, $R^4$, and $R^5$ represent hydrogen; chlorine; fluorine; alkyl which optionally is substituted with halogen, said alkyl having been selected from methyl, ethyl, propyl, butyl, pentyl, isopropyl, isobutyl, sec-butyl, t-butyl, neopentyl; trifluoromethyl; triethylsilyl; and
n represents an integer from 0 to 2.

Preferred tellurium molecules disclosed in the present invention include without limitations: Te(pentane-2,4-diketiminato)$_2$, Te(N,N'-dimethylpentane-2,4-diketiminato)$_2$, Te(N,N'-diethylpentane-2,4-diketiminato)$_2$, Te(N,N'-diisopropylpentane-2,4-diketiminato)$_2$, Te(pentane-2,4-ketoiminato)$_2$, Te(N-methylpentane-2,4-ketoiminato)$_2$, Te(N-ethylpentane-2,4-ketoiminato)$_2$, and Te(N-isopropylpentane-2,4-ketoiminato)$_2$ Tellurium β-diketimines may by synthesized from the reaction of the tetrafluoroborate salt of the diketimine and the tellurium halide, similar to the procedure outlined by McGeachin (Can. J. Chem. 1968, 46 1903-1912) for nickel β-diketimines. Tellurium β-ketoimines may by synthesized from the reaction of the ketoimine salt with a tellurium halide, similar to the procedure outlined by McGeachin (Can. J. Chem. 1968, 46 1903-1912) for nickel β-diketimines.

The tellurium metal-organic compounds may be utilized to form a tellurium-containing film on a substrate. The tellurium metal-organic compounds may be mixed with another metal source to deposit a film containing both tellurium and the other metal on a substrate. The tellurium-containing film and the film containing both tellurium and another metal may both be formed by deposition techniques known in the art.

The type of substrate upon which the precursor will be deposited will vary depending on the final use intended. In some embodiments, the substrate may be chosen from oxides which are used as dielectric materials in MIM, DRAM, FeRam technologies or gate dielectrics in CMOS technologies (for example, HfO based materials, TiO$_2$ based materials, ZrO$_2$ based materials, rare earth oxide based materials, ternary oxide based materials, etc.) or from nitride-based films (for example, TaN) that are used as an oxygen barrier between copper and the low-k layer. Other examples of substrates upon which the tellurium-containing film may be coated using the process of the present invention include, but are not limited to, solid substrates such as metal substrates (for example, Ru, Al, Ni, Ti, Co, Pt and metal silicides, such as TiSi$_2$, CoSi$_2$, and NiSi$_2$); metal nitride containing substrates (for example, TaN, TiN, WN, TaCN, TiCN, TaSiN, and TiSiN); semiconductor materials (for example, Si, SiGe, GaAs, InP, diamond, GaN, and SiC); insulators (for example, SiO$_2$, Si$_3$N$_4$, HfO$_2$, Ta$_2$O$_5$, ZrO$_2$, TiO$_2$, Al$_2$O$_3$, and barium strontium titanate); or other substrates that include any number of combinations of these materials. The actual substrate utilized will also depend upon the specific precursor embodiment utilized. In many instances though, the preferred substrate utilized will be selected from TiN, Ru, and Si type substrates.

The tellurium metal-organic compound is introduced into a reaction chamber containing a substrate. The reaction chamber may be any enclosure or chamber of a device in which deposition methods take place, such as, without limitation, a cold-wall type reactor, a hot-wall type reactor, a single-wafer reactor, a multi-wafer reactor, or other such types of deposition systems.

The substrate may be heated to a sufficient temperature to obtain the desired tellurium-containing film at a sufficient growth rate and with desired physical state and composition. A non-limiting exemplary temperature range to which the substrate may be heated includes from 150° C. to 600° C. Preferably, the temperature of the substrate remains less than or equal to 450° C. The pressure in the reaction chamber is controlled to obtain the desired tellurium-containing film at sufficient growth rate. A non-limiting exemplary pressure range in the reaction chamber is from 1 mTorr level to 100 Torr or higher.

The tellurium metal-organic compound may be fed in liquid state to a vaporizer where it is vaporized before it is introduced into the reaction chamber. Prior to its vaporization, the tellurium metal-organic compound may be mixed with one or more solvents, one or more metal sources, a mixture of one or more solvents and one or more metal sources, and/or a stabilizer. The solvents may be selected from the group consisting of octane, hexane, pentane, tetramethylsilane, or others. The metal source may include any metal precursors now known or later developed. Known stabilizers may be necessary depending on the structure of the tellurium metal-organic compound.

Alternatively, the tellurium metal-organic compound may be vaporized prior to introduction into the reaction chamber by passing a carrier gas into a heated container containing the tellurium metal-organic compound. The container is preferably heated to a temperature that permits the tellurium metal-organic compound to be in its liquid phase and to have a sufficient vapor pressure. The carrier gas may include, but is not limited to, Ar, He, $H_2$, $N_2$, or mixtures thereof. The tellurium metal-organic compound may be mixed in the container with a solvent, another metal source, or a mixture thereof. The container may be heated to temperatures in the range of, for example, 0-100° C. Those skilled in the art recognize that the temperature of the container may be adjusted to control the amount of tellurium metal-organic compound vaporized.

In addition to mixing the tellurium metal-organic compound with solvents, metal sources, and stabilizers prior to introduction into the reaction chamber, the tellurium metal-organic compound may be mixed with reactant species inside the reaction chamber. Exemplary reactant species include, without limitation, $H_2$, TMA or an aluminum-containing precursor, TBTDET, TAT-DMAE, PET, TBTDEN, PEN, lanthanide-containing precursors such as $Ln(tmhd)_3$, and any combination thereof.

When the desired tellurium-containing film also contains nitrogen, such as, for example and without limitation, tellurium nitride or tellurium carbo-nitride, the reactant species may include a nitrogen source which is selected from, but not limited to, nitrogen ($N_2$), ammonia, hydrazine and alkyl derivatives, N-containing radicals (for instance N., NH., $NH_2$.), NO, $N_2O$, $NO_2$, amines, and any combination thereof.

When the desired tellurium-containing film also contains carbon, such as, for example and without limitation, tellurium carbide or tellurium carbo-nitride, the reactant species may include a carbon source which is selected from, but not limited to, methane, ethane, propane, butane, ethylene, propylene, t-butylene, isobutylene, $CCl_4$, and any combination thereof.

When the desired tellurium-containing film also contains silicon, such as, for example and without limitation, tellurium silicide, tellurium silico-nitride, tellurium silicate, tellurium silico-carbo-nitride, the reactant species may include a silicon source which is selected from, but not limited to, $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, trisilylamine, disiloxane, trisilylamine, disilane, trisilane, an alkoxysilane $SiH_x(OR^1)_{4-x}$, a silanol $Si(OH)_x(OR^1)_{4-x}$ (preferably $Si(OH)(OR^1)_3$; more preferably $Si(OH)(OtBu)_3$, an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS, BTBAS, and/or BDEAS), and any combination thereof. The targeted film may alternatively contain Germanium (Ge), in which case the above-mentioned Si-containing reactant species could be replaced by Ge-containing reactant species.

When the desired tellurium-containing film also contains another metal, such as, for example and without limitation, As, Sb, Bi, Sn, Pb, the reactant species may include a metal source which is selected from, but not limited to, metal alkyls such as $SbR^{i'}_3$ or $SnR^{i'}_4$ (wherein each $R^i$ is independently H or a C1-C6 carbon chain, either linear, branched, or cyclic), metal alkoxides such as $Sb(OR^i)_3$ or $Sn(OR^i)_4$ (where each $R^i$ is independently H or a C1-C6 carbon chain, either linear, branched or cyclic), and metal amines such as $Sb(NR^1R^2)(NR^3R^4)(NR^5R^6)$ or $Ge(NR^1R^2)(NR^3R^4)(NR^5R^6)(NR^7R^8)$ (where each $R^i$ is independently H or a C1-C6 carbon chain or an trialkylsilyl group, either linear, branched, or cyclic), and any combination thereof.

The tellurium metal-organic compound and the reactant species may be introduced into the reaction chamber simultaneously (chemical vapor deposition), sequentially (atomic layer deposition), or in other combinations. For example, the tellurium metal-organic compound may be introduced in one pulse and two additional metal sources may be introduced together in a separate pulse [modified atomic layer deposition]. Alternatively, the reaction chamber may already contain the reactant species prior to introduction of the tellurium metal-organic compound. The reactant species may be passed through a plasma system localized remotely from the reaction chamber, and decomposed to radicals. Alternatively, the tellurium metal-organic compound may be introduced to the reaction chamber continuously while other metal sources are introduced by pulse (pulsed-chemical vapor deposition).

The resulting tellurium-containing films may include SbTe, CdTe, $Ge_2Sb_2Te_5$, $InGe_2Te_2$, AsSbTe, CrSbTe, MoSbTe, or $M^1_xSb_yTe_z$, with $M^1$ being selected from but not limited to germanium, chromium, or arsenic.

EXAMPLES

The following examples illustrate deposition methods using the disclosed tellurium metal-organic compound. The examples are not intended to be all inclusive and are not intended to limit the scope of disclosure described herein.

FIG. 1 is a flow chart of one exemplary deposition process through which the disclosed tellurium metal-organic compound may proceed to deposit a tellurium containing film on a substrate. In step 1, the tellurium metal organic compound is vaporized. The vaporized tellurium metal organic compound is transported in a gas phase to a reaction chamber in step 2. The tellurium metal-organic compound is mixed with a reactant species in step 3. In step 4, the metal-organic compound/reactant species mixture is contacted to a substrate at appropriate flow rates, pressure and temperature conditions to deposit a tellurium-containing film.

Figure 2:
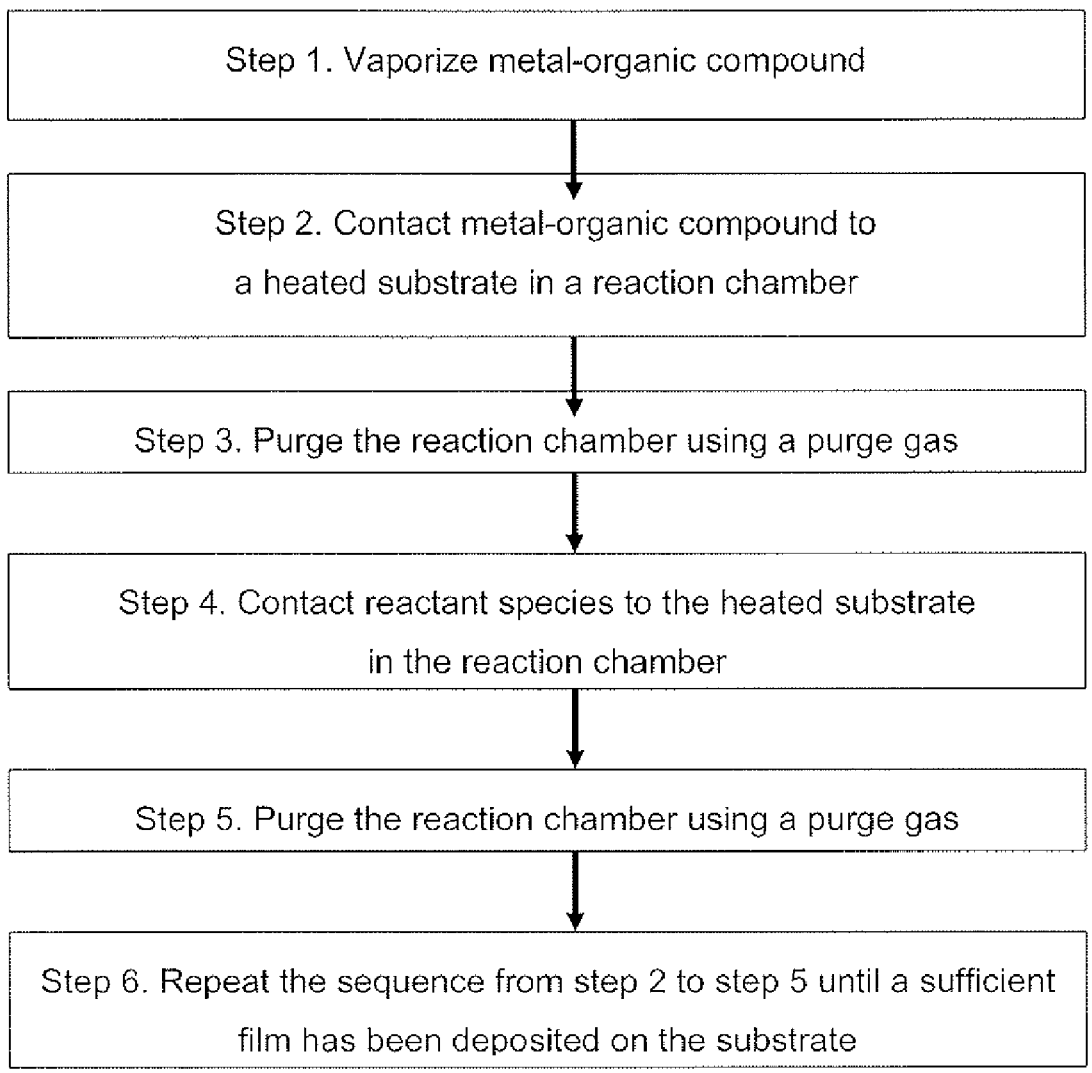
FIG. 2 is a flow chart of a second exemplary deposition process through which the disclosed tellurium metal-organic compound may proceed.

FIG. 2 is a flow chart of a second exemplary deposition process through which the disclosed tellurium metal-organic compound may proceed. As in FIG. 1, the first step is to vaporize the tellurium metal-organic compound. The vaporized tellurium metal-organic compound is contacted to a heated substrate in the reaction chamber in step 2. In step 3, the reaction chamber is purged using a purge gas. A reactant species is contacted to the heated substrate in step 4. In step 5, the reaction chamber is again purged using a purge gas, which may be the same or different from the purge gas in step 3. Step 6 instructs to repeat steps 2 through 5 until a sufficient film has been deposited on the substrate.

In a third exemplary process, the tellurium metal-organic compound is introduced into the reaction chamber in vapor phase. The reaction chamber contains a substrate at a temperature between 100 to 500° C., preferably between 150 and 350° C. A reactant species is introduced into the reaction chamber and mixed with the tellurium metal-organic compound. The resulting mixture is contacted with the substrate to deposit a tellurium-containing film.

In a fourth exemplary process, the tellurium metal-organic molecule is used for atomic layer deposition of tellurium-containing films. The tellurium metal-organic molecule, a possible second metal source, and a reactant species are introduced sequentially in the reaction chamber. The pressure of the reaction chamber is selected in the range from 1 mTorr to 100 Torr. Preferably, the pressure is between 1 and 10 Torr. A purge gas is introduced between the pulse of the tellurium metal-organic compound and the reactant species pulse. The purge gas can be selected without limitation from the group consisting of $N_2$, Ar, He. The tellurium metal-organic compound, purge gas, and reactant species pulse duration is approximately between 0.1 and 100 seconds (s). Preferably the pulse duration lasts between 0.5 and 10s.

In a fifth exemplary, process, Te β-diketimines are used to deposit a SbTe film. bis(pentane-2,4-diketiminato)Tellurium (II) [Te(pda)$_2$] is stored in a container. The container is heated at 25° C. and $N_2$ is used as carrier gas at a flow of 50 sccm. The pressure of the container is controlled at 50 Torr. The substrate is heated at 350° C. During a first step, Te(pda)$_2$ is introduced into the reaction chamber during 2s. A $N_2$ purge of 5s is performed afterwards as second step. As third step, a pulse of Sb(iPr)$_3$ is then introduced into the reaction chamber during 2s, followed by a 2s $N_2$ purge as fourth step. All four steps are repeated 100 times to obtain a SbTe film. Self-limited atomic layer deposition is obtained.

In place of the Sb-containing precursor [Sb(iPr)$_3$] above, experiments may be performed with precursors containing a group V or group VI metal to produce a film containing both Te and the group V or VI metal.

In a sixth exemplary process, Te β-diketimines are used to deposit a GeSbTe film, such as Ge$_2$Sb$_2$Te$_5$. Te(pda)$_2$ is stored into a container. The container is heated at 25° C. and $N_2$ is used as carrier gas at a flow of 50 sccm. The pressure the container is controlled at 50 Torr. The substrate is heated at 350° C. During a first step, Te(pda)$_2$ is introduced into the reaction chamber during 2s. A $N_2$ purge of 5s is performed afterwards as second step. As third step, a pulse of Sb(iPr)$_3$ is then introduced into the reaction chamber during 2s, followed by a 2s $N_2$ purge as fourth step. As a fifth step, Ge(iBu)$_4$ is introduced into the reaction chamber during 2s, followed by a 2s $N_2$ purge as a sixth step. All six steps are repeated 100 times to obtain a GeSbTe film, such as Ge$_2$Sb$_2$Te$_5$. Self-limited atomic layer deposition is obtained.

In place of the Sb-containing precursor [Sb(iPr)$_3$], the Ge-containing precursor [Ge(iBu)$_4$], or both, experiments may be performed with precursors containing a group V and group VI metal to produce a film containing Te in combination with Sb, Ge, the group V, and/or the group VI metal.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A metal-organic compound comprising the formula $R_m$—Te-$L_n$ wherein:
R represents substituted β-diketiminato of the general formula $R^1C(NR^4)CR^2 C(NR^5)R^3$ or substituted β-ketoiminato of the general formula $R^1COCR^2 C(NR^4)R^3$, $R^1$ and $R^3$ may be the same or different and represent a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl substituted phenyl or organosilyl, and $R^2$, $R^4$, and $R^5$ may be the same or different and represent hydrogen, halogen, a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl, or an organosilyl;
each L is independently selected from the group consisting of a hydrocarbon, an oxygen-containing hydrocarbon, a nitrogen-containing hydrocarbon, an amine or polyamine, a bipyridine, a heterocycle containing oxygen or nitrogen, and combinations thereof;
m represents an integer from 1 to 4; and
n represents an integer from 0 to 4.

2. The metal organic compound of claim 1, wherein:
R is $(R^1COCR^2C(NR^4)R^3)$;
$R^1$ and $R^3$ are methyl; and
$R^4$ is isopropyl.

3. The metal-organic compound of claim 1, wherein
R is $(R^1C(NR^4)CR^2C(NR^5)R^3)$;
$R^1$ and $R^3$ are methyl; and
$R^4$ and $R^5$ are isopropyl.

4. The metal organic compound of claim 1, wherein R is $R^1C(NR^4)CR^2 C(NR^5)R^3$, m is 2, n represent an integer from 0 to 2, and having the following formula:

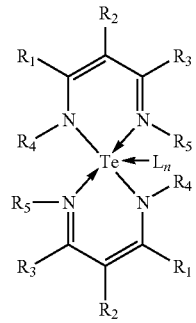

5. The metal organic compound of claim 4, wherein $R^1=R^3$ and are methyl, $R^2$ is H, and $R^4=R^5$ and are selected from the group consisting of H, methyl, ethyl, and isopropyl.

6. The metal organic compound of claim 1, wherein R is $R^1COCR^2 C(NR^4)R^3$, m is 2, n represent an integer from 0 to 2, and having the following formula:

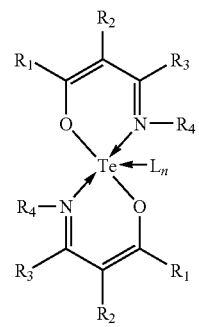

7. The metal organic compound of claim 6, wherein $R^1=R^3$ and are methyl, $R^2$=H, and $R^4$ is selected from the group consisting of H, methyl ethyl, and isopropyl.

8. A method of forming a tellurium-containing film on a substrate, the method comprising:
  providing a reaction chamber having at least one substrate disposed therein;
  introducing at least one metal-organic compound into the reaction chamber, wherein the metal-organic compound has the general formula $R_m$—Te-$L_n$, wherein:
    R represents substituted β-diketiminato of the general formula $R^1C(NR^4)CR^2 C(NR^5)R^3$ or substituted β-ketoiminato of the general formula $R^1COCR^2 C(NR^4)R^3$,
    $R^1$ and $R^3$ may be the same or different and represent a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl substituted phenyl, or an organosilyl, and $R^2$, $R^4$, and $R^5$ may be the same or different and represent hydrogen, halogen, a linear or branched alkyl having from 1 to 5 carbon atoms, a halogen-substituted linear or branched alkyl having from 1 to 7 carbon atoms, an alkylamide having from 1 to 4 carbons, an alkoxide having from 1 to 4 carbons, an aryl, or an organosilyl;
    each L is independently selected from the group consisting of a hydrocarbon, an oxygen-containing hydrocarbon, an amine or polyamine, a bipyridine, a heterocycle containing oxygen or nitrogen, or any combination thereof;
    m represents an integer from 1 to 4; and
    n represents an integer from 0 to 4; and
  contacting the metal-organic compound and the substrate to form a tellurium-containing film on at least one surface of the substrate using a deposition process.

9. The method of claim 8, further comprising:
  providing at least one reactant species into the reaction chamber with the metal-organic compound to form a reaction mixture;
  contacting the reactant mixture with the substrate.

10. The method of claim 8, further comprising:
  providing at least one reactant species into the reaction chamber; and
  reacting the metal-organic compound with the reactant species.

11. The method of claim 10, wherein the metal-organic compound and the reactant species are either introduced at least partially simultaneously as in a chemical vapor deposition process, or are introduced at least partially sequentially as in an atomic layer deposition process.

12. The method of claim 8, wherein a temperature of the reaction chamber ranges between 100 to 500° C.

13. The method of claim 12, wherein the temperature of the reaction chamber ranges between 150 and 350° C.

14. The method of claim 8, wherein the deposition process is a chemical vapor deposition process.

15. The method of claim 8, wherein the deposition process is an atomic layer deposition process having a plurality of deposition cycles.

* * * * *